United States Patent
Sisskind et al.

(10) Patent No.: US 6,355,051 B1
(45) Date of Patent: Mar. 12, 2002

(54) GUIDEWIRE FILTER DEVICE

(75) Inventors: Steven J. Sisskind, Los Angeles; Dac Vu, Placentia, both of CA (US)

(73) Assignee: Bioguide Consulting, Inc., Denver, CO (US)

( * ) Notice: Subject to any disclaimer, the term of this patent is extended or adjusted under 35 U.S.C. 154(b) by 0 days.

(21) Appl. No.: 09/601,673

(22) PCT Filed: Mar. 4, 1999

(86) PCT No.: PCT/US99/05163

§ 371 Date: Dec. 28, 2000

§ 102(e) Date: Dec. 28, 2000

(87) PCT Pub. No.: WO99/44510

PCT Pub. Date: Sep. 10, 1999

(51) Int. Cl.[7] .............................................. A61M 29/00
(52) U.S. Cl. ...................................................... 606/200
(58) Field of Search ................................ 606/200, 108, 606/159, 195, 198, 113, 114

(56) References Cited

U.S. PATENT DOCUMENTS

| | | | |
|---|---|---|---|
| 5,100,423 A | * 3/1992 | Fearnot | 606/159 |
| 6,022,336 A | 2/2000 | Zadno-Azizi et al. | 604/96 |
| 6,053,932 A | 4/2000 | Daniel et al. | 606/200 |
| 6,059,814 A | * 5/2000 | Ladd | 606/200 |
| 6,136,016 A | * 10/2000 | Barbut et al. | 606/200 |
| 6,142,987 A | 11/2000 | Tsugita | 604/500 |
| 6,152,946 A | 11/2000 | Broome et al. | 606/200 |
| 6,165,200 A | * 12/2000 | Tsugita et al. | 606/200 |
| 6,168,579 B1 | 1/2001 | Tsugita | 604/96.01 |
| 6,171,328 B1 | 1/2001 | Addis | 606/200 |
| 6,179,859 B1 | 1/2001 | Bates et al. | 606/200 |
| 6,190,332 B1 | 2/2001 | Muni et al. | 600/585 |
| 6,277,138 B1 | 8/2001 | Levinson et al. | 606/200 |
| 6,277,139 B1 | 8/2001 | Levinson et al. | 606/200 |

* cited by examiner

Primary Examiner—Olik Chaudhuri
Assistant Examiner—(Vikki) Hoa B. Trinh
(74) Attorney, Agent, or Firm—Christie, Parker & Hale, LLP

(57) ABSTRACT

A guidewire filter (10) has an elongate hollow tube (12) with a proximal end, a distal end, an inside, an outside surface, and a lumen formed therethrough. The hollow tube (12) has a plurality of longitudinal slots (14) forming a plurality of longitudinal rib portions (16) near the distal region of the hollow tube (12). An actuating wire (24) with a proximal end, and a distal end is provided. Filter material (20) is positioned within the lumen in the hollow tube (12). An activation handle (38) on the proximal end of the device (10) is provided for pulling the actuating wire (24) relative to the hollow tube (12).

19 Claims, 7 Drawing Sheets

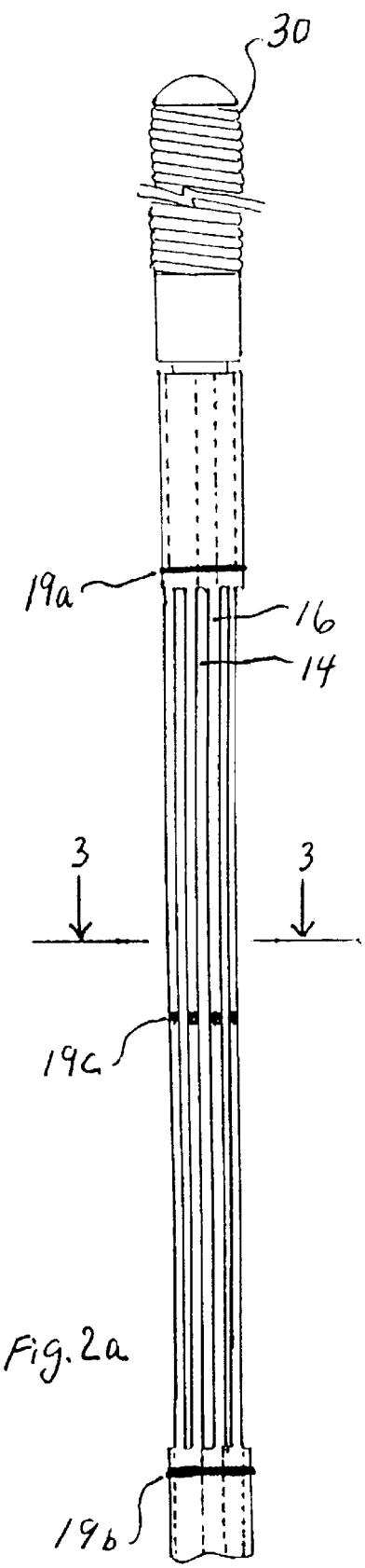

GUIDEWIRE FILTER DEVICE

BACKGROUND OF THE INVENTION

1. Field of the Invention

The present invention relates to the field of guidewires, and more particularly to a blood filter guidewire device to be used in percutaneous carotid angioplasty procedures for treatment of carotid artery stenosis and any other hollow conduit disorders.

2. Description of the Related Art

Carotid artery stenosis is a narrowing of the carotid artery due to build-up of atheromatous plaque. Carotid artery stenosis is the most common cause of stroke and stroke is the third leading cause of death and the number one cause of long-term disability in the United States. The standard treatment for patients with carotid artery stenosis is carotid endarterectomy (CEA). CEA is a surgical procedure that involves open exposure and incision of the carotid artery followed by removal of the atheromatous plaque. Currently, physicians perform 120,000 CEA procedures annually in the United States.

A newer procedure called percutaneous transluminal angioplasty (PTA) of the carotid artery has been advocated as an alternative to CEA for the treatment of carotid artery stenosis. The procedure involves insertion of a balloon tipped catheter into the stenotic region of the carotid artery. The physician inflates the balloon against the stenotic artery wall to dilate the arterial lumen, thereby improving blood flow through the vessel.

PTA may be a viable alternative to and/or possible replacement of CEA. However, preliminary published results of PTA procedures reveal higher stroke/death rates compared to those achieved with CEA. The increased stroke rates result from the dislodgment of intra-arterial embolic material during the angioplasty procedure.

There has been some work done on devices to deal with this situation. For example, U.S. Pat. No. 4,723,549 to Wholey et al. describes a catheter designed to slide over a guidewire for dilating occluded or stenotic blood vessels. The Wholey et al. device is a balloon catheter with a collapsible filter portion. The collapsible filter is deployed by inflating a filter balloon positioned near the distal end of the catheter. The catheter also has a dilating balloon set back proximally from the filter balloon for compressing the stenosis. The collapsible filter device comprises a plurality of resilient ribs secured to the catheter at the distal end of the catheter and extending generally longitudinally toward the dilating balloon. Inflation of a filter balloon pushes the ribs outwardly against the vessel wall to stretch filter material secured to the ribs across the vessel to form a cup shaped trap. This filter is supposed to capture fragments of a stenosis loosened by the dilating balloon. Upon deflation of the filter balloon, the resilient ribs retract against the catheter to retain the trapped fragments during withdrawal of the catheter. In the preferred embodiment of the Wholey et al. device, the proximal ends of the ribs projecting generally toward the dilating balloon are moveably secured to a ring that slides along the outside surface of the catheter. In use, the cup-shaped trap filter is extended and then the dilating balloon is inflated. Blood flow established by deflation of the dilating balloon carries stenosis fragments into the filter.

There are several shortcomings with the Wholey et al. catheter. For example, in the first embodiment, nothing positively moves the ribs and the carried filter to the retracted position against the walls of the catheter. Furthermore, the free ends of the ribs could very well entangle with each other, or possibly damage the vessel walls, and/or inadvertently release captured particles from the trap filter. In the second embodiment, a slideable ring moveably retains proximal ends of the ribs. This second ring is slidably positioned on the outside surface of the catheter. In both embodiments, all the filter components are located to the exterior or on the outside of a rather large catheter. During withdrawal of the catheter, there is a possibility that free proximal ends of the ribs (or the slideable ring) can be caught on the vessel walls and thus reopen the trap filter. Moreover, the Wholey et al. catheter, by integrating the trap filter into the design of the catheter gives a physician less flexibility in where the filter is to be positioned relative to the stenosis. Indeed, it would appear that the excessively complex design of Wholey et al would make the device too large to fit and function within the carotid artery.

U.S. Pat. No. 5,695,519 to Summers et al. discloses a distal intravascular filter for filtering blood and entrapping and retaining embolic debris. The intravascular filter includes a small diameter hollow guide wire or tube capable of percutaneous placement beyond a carotid stenosis. The distal portion of the tube includes a filter mounted thereon. The filter is deployable from a tightly closed configuration to an open circumference for filtering embolic material from the bloodstream. The filter is deployable between open and closed positions by manipulation of an actuating wire extended from the filter and out the proximal end of the tube. An examination of the design would indicate that at least one major problem with the Summers et al. device is that the actuating wires are too thin. Deployment of the filter mechanism requires pushing the actuating wires along a column of about 175-cm in length. The wires cannot support the force necessary to properly deploy the filter because they cannot be made thick enough to perform their function and constrain to the necessary dimensions of the hollow tube or wire. A second problem is that once the filter is deployed, there is no way to assure that the filter will stay open and be secured against the arterial wall. The system relies on the blood flow to keep it open, which may not be sufficient to maintain an open filter, particularly in a stenotic carotid artery. Thirdly, because of a multitude of moving parts, the system would likely be expensive to produce and difficult to assemble, and would likely encountering similar problems of as that of the Wholey et al catheter, including inability to fit all the parts into a tight space.

There accordingly remains a need for a guidewire filter device that can be used in lieu of conventional guideware during percutaneous carotid angioplasty procedures to capture any dislodged intra-arterial embolic material.

SUMMARY OF THE INVENTION

One object of the invention is to provide a guidewire filter device that is compatible with current carotid angioplasty balloon catheter systems, viz., can be used in place of conventional guidewires.

Another object of the invention is to provide a guidewire filter device in which filter or mesh material is located inside of the guidewire filter rather than outside the guidewire or catheter shaft to provide a relatively smooth exterior surface. This enables smoother passage of the device within the artery and may decrease the risk of possible fragmentation and subsequent emboli of plaque particles of the stenotic lesion and/or damage to the arterial wall.

Yet another object of the invention is to provide a guidewire filter device including a ribbed cage/basket design that expands to seat against the arterial wall, forming a self-supporting and non-collapsing seal for the filter mesh against the arterial wall. Blood and particles will accordingly be required to travel through the filter mesh rather than around it. While the blood and its components will be able to freely travel through the filter mesh, those particles that are larger than the pore size of the filter mesh, e.g. intra-arterial embolic material, will be prevented from traveling further and will be effectively captured.

A further object of the invention is to provide a guidewire filter device in which the filter is deployed by pulling (rather than by pushing) on an actuating wire allowing use of a thinner wire.

A final object of the invention is to provide a guidewire filter device that is simple in design, involves relatively few parts, is economical to manufacture, and that is reliable and safe in its operation.

These and other aspects of the present invention are afforded by providing a guidewire filter device that comprises a distal filter element contained within a hollow tube/wire housing. The outer diameter of the device will preferably not exceed 0.13 cm (0.050 inches) and even more preferably will not exceed 0.0889 cm (0.035 inches) so as to be compatible with current carotid angioplasty balloon catheter systems. For other uses involving larger hollow conduit disorders, a large size can be utilized. The length of the guidewire will preferably be approximately 150 to 190 cm to allow for catheter exchange during the PTA procedure, but can be of different lengths as required. The filter element or portion is located at the distal end of the device. There are longitudinal slots or "ribs" located circumferentially around the filter housing. The slots are ideally oriented longitudinally, but can be oriented spirally or in other orientations. Filter mesh material is located inside the filter element and is attached to the inner distal section of the ribs. Alternately, the filter material can be affixed to outer surfaces of the ribs, or can even be sandwiched between the outer ribs and outer rib overlay portions to help secure the filter material in place. In yet a further embodiment, the ribs themselves can be sandwiched by a section of an inner filter material and a section of outer filter material, with the inner and outer filter materials being affixed to inner and outer surfaces, respectively, of the ribs. These inner and outer filters can also optionally affixed at least partly together. In this double material embodiment, the inner and outer filter materials could be made of thinner filter material so that the inner filter material can be made to better fit into the interior surface of the guidewire. An actuating wire attaches to the distal most end of the filter housing and passes through the entire length of the guidewire and out the proximal end. A handle/remote activation device attached to the proximal end attaches to and operates the actuating guidewire.

During a PTA procedure, a physician will use fluoroscopy to steer the guidewire filter device of the invention into place in the carotid artery distal to the stenotic lesion. The physician will then place the balloon angioplasty catheter over the guidewire filter device of the invention. The physician will then use a handle/remote activation device at the proximal end of the device to deploy the filter element or portion at the distal end of the device. The ribs of the filter element will expand into a cage/basket formation. As the cage opens, the folded filter mesh material will open along with the ribs, forming an inverted cup-shaped trap for any embolic material broken loose during the balloon angioplasty procedure. The ribs push against the inner arterial wall, forming a tight seal with the inner arterial wall and the expanded filter mesh covers the opening of the artery. The physician then performs the PTA procedure. After the procedure, the physical will collapse the filter assembly either by withdrawing the guidewire filter housing into the distal balloon catheter tip, and/or by using the handle/remote activation device to release tension on the actuating wire to allow the ribs to reflex back down. Any embolic material resting against the inside of the filter mesh will thus be captured. When the filter element is retracted and closed, any embolic material will be withdrawn from the arteries along with the guidewire filter device of the invention.

The new design of the invention thus has a unique features that render it significantly different and markedly better than other devices used to perform similar functions. The innovations and improvements intrinsic to the current guidewire filter design include the following:

1. The design allows for an accurate and reliable means to activate and deactivate the guidewire filter device.
2. The filter material is preferably stored and operated inside the guidewire filter rather than outside the guidewire or catheter shaft. This allows for maintenance of a smooth exterior, enabling easier movement of the device within the artery and decreases the risk of possible damage to the arterial wall.
3. The ribbed cage/basket design expands to seat on the inner arterial wall, forming a self-supporting and non-collapsing seal for the filter against the inner arterial wall. Accordingly, blood and loose particles will be forced to travel through the filter mesh rather than around it. Those particles that are larger than the filter mesh will be captured and prevented from traveling further by the filter mesh.
4. The filter deploys by pulling the actuating wire rather than pushing on it, allowing use of a narrow gauge wire that is compatible with the inner lumen of the guidewire.
5. The design is simple, reliable, involves relatively few parts, and enables an efficient and low cost process to be used to manufacture the device.

BRIEF DESCRIPTION OF THE DRAWINGS

The appended drawings demonstrate the above features, advantages and objects of the present invention.

FIG. 2a is a partial side view of the invention of FIG. 1 showing the guidewire filter portion in the closed position with radiopaque markers.

FIG. 2b is a partial side view of the invention of FIG. 1 showing the guidewire filter portion in the closed position with radiopaque rib portions.

DETAILED DESCRIPTION OF THE PREFERRED EMBODIMENTS

Figure 1:
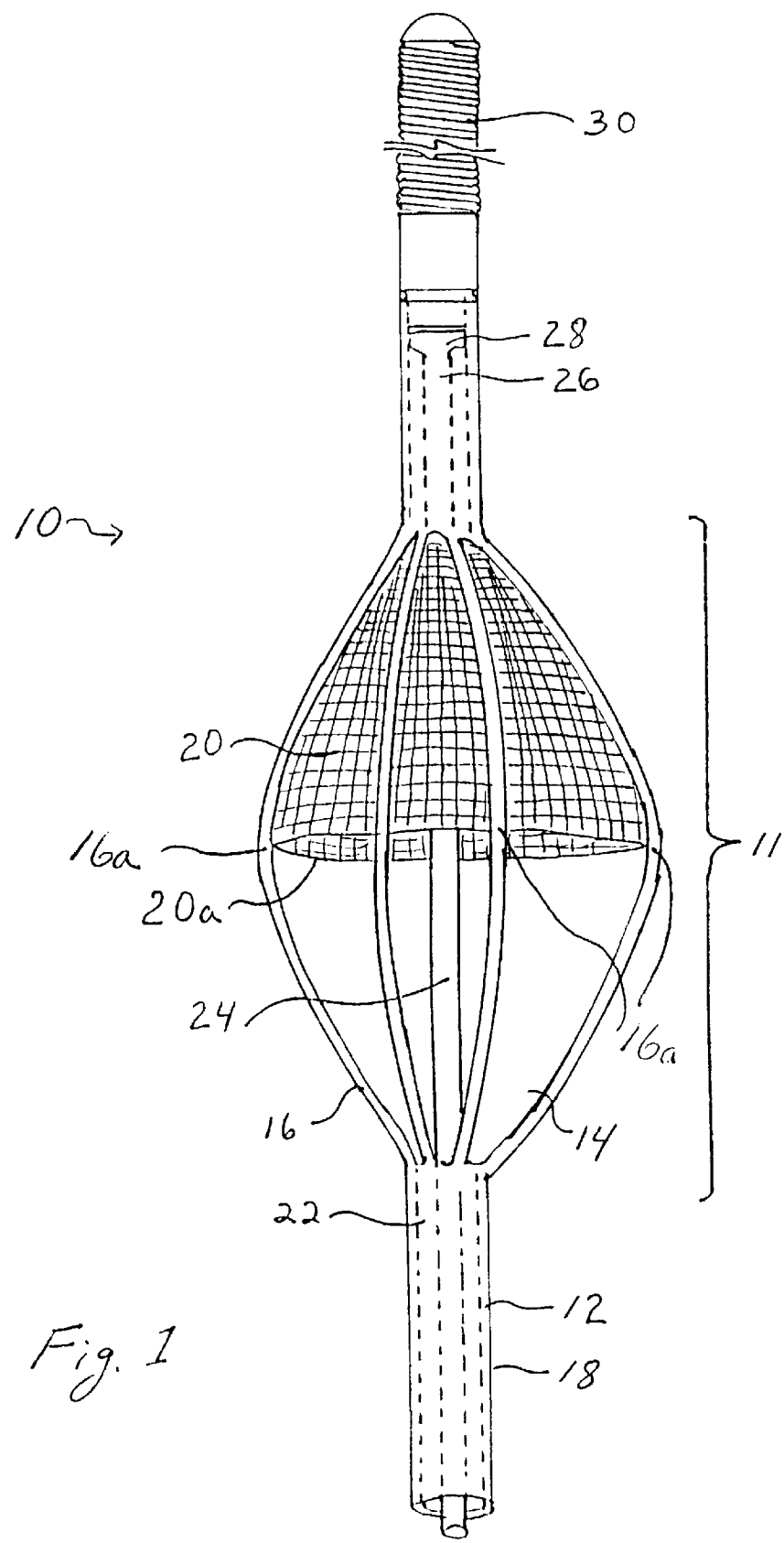
FIG. 1 is a partial perspective views of a first embodiment the invention showing the guidewire filter portion of the device in the open position.

Referring to FIG. 1, the guidewire filter 10 on the invention is shown in its open position, forming a filter basket 11. Guidewire filter 10 consists of an outer hollow tube 12 with a plurality of elongate slots 14 formed circumferentially around and in a longitudinal orientation to define rib portions 16 (see also FIG. 2a). Outer hollow tube 12 is composed of a shape memory alloy, or other metal or composite material (or any other known materials) that has the appropriate strength and shape characteristics to conform to the filter basket requirements. Outer hollow tube 12 protects the guidewire filter 10 while the filter 10 is manipulated into position in the arteries. Because the outer hollow tube 12 is smooth on its exterior surface 18, it enhances the maneuverability of the guidewire filter 10 as it is being manipulated through arteries, and when positioned as required. FIG 2a shows slots 14 formed in a longitudinal orientation to form longitudinal rib portions 16. Optionally, radiopaque markers 19a and 19b can be positioned on the device adjacent to distal and proximal ends, respectively, of the slots 14 and 16. By measuring the spacing of these radiopaque markers 19a and 19b during a procedure, the physician can determine (e.g. by fluoroscopy) to what extent the filter basket 11 is expanded or contracted. Additional radiopaque markers 19c can also be formed near the center points of the rib portions 16 so that the physician can determine the greatest point of expansion of the filter basket 11 against the inside wall of the vessels when expanded (not shown.) In lieu of specific radiopaque markers, all or portions of the rib portions 16 themselves can be painted, plated, and/or imbued with radiopaque material (e.g. gold, platinum, etc.) as best shown in FIG. 2b.

Figure 3:
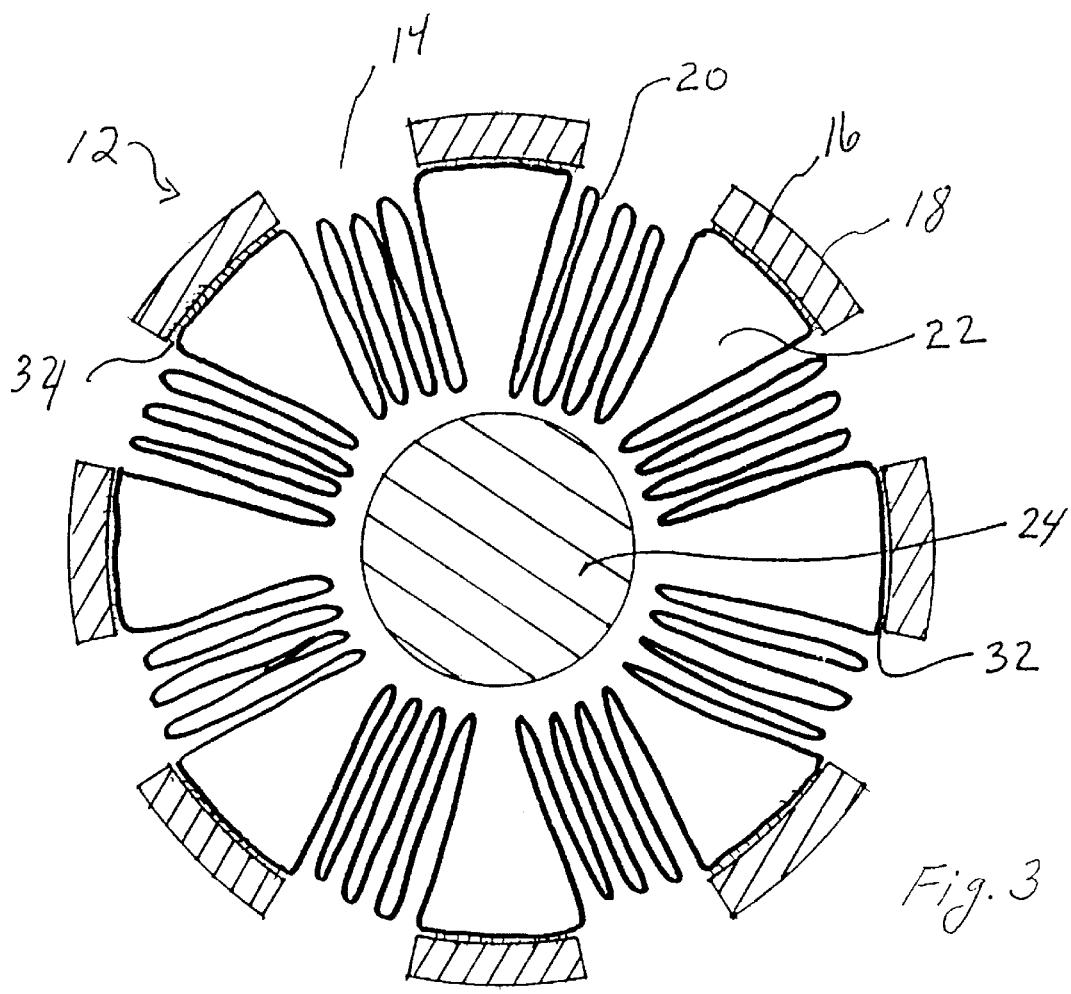
FIG. 3 is a cross-sectional view through view lines 3—3 of FIG. 2.

Referring to FIGS. 1 and 3, filter material 20 is attached to the inside of at least some of and preferably all of ribs 16 and filter material 20 expands out with filter basket 11 when the mechanism is deployed. In the closed condition as shown in FIGS. 2 and 3, filter material 20 is stored in the space 22 between outer tube 12 and the inner actuating core wire 24. The space 22 is a lumen in the hollow tube 12.

As shown in FIG. 1, the filter material 20 is affixed to about the distal most one half of the rib portions 16 in the form of an inverted cup-shaped net when expanded. Indeed, the edge 20a of the filter material 20 can preferably be in line with the most expanded region or points 16a of the rib portions so that when the filter basket 11 is expanded in an artery, a good seal will be formed against the arterial wall so that any fragments that might have broken free and are floating in the blood are captured by the filter basket 11. As shown in FIG. 3, the filter material 20 is affixed to the inside walls 32 of ribs 16, e.g. by adhesives 34 or other means.

Filter material 20 is shown as being folded to remain within space 22 between the inner surface 32 of hollow tube 12 and actuating wire 24. However, as noted above, by use of flexible, stretchable, elastic, and resilient filter material, folding of the filter material can be reduced or eliminated. While an arrangement with eight rib portions 16 is shown, the device 10 can be made with a greater or lesser number of rib portions 16.

The filter material 20 is selected to pass vital elements in the blood stream (such as red blood cells, white blood cells and platelets) while trapping dislodged embolic material from the carotid angioplasty procedure. The filter 10 configuration will be designed to minimize interruption of blood flow to the brain. In the preferred embodiment, the filter material 20 is composed of an elastic mesh material that expands and contracts with the cage/basket 11. In an alternate embodiment, the filter material 20 is composed of a non-elastic mesh material that is folded inside the filter housing and unfolds as the basket 11 opens (as is best shown in FIG. 3.) Another option is to design a drop in filter cartridge to reduce the complexity of the filter design and manufacturing costs (not shown).

As shown in FIGS. 1 and 3, the actuating wire 24 is shown passing through passageway 22 inside the outer hollow tube 12. The actuating wire 24 provides the leverage point for activating the filter basket 11. The actuating wire 24 comprises stainless steel or other metal or composite materials with the appropriate strength and shape characteristics to conform to the actuating wire specifications. The actuating wire 24 is permanently attached (e.g. by adhesives or otherwise) at its distal end 26 to a position 28 inside outer tube 12 that is distal to the rib portions 16. By pulling on the actuating wire 24 (and/or pushing on the outer hollow tube 12), the distal end of outer hollow tube 12 will cause rib portions 16 and the carried filter material 20 to expand outward, forming the cage or basket shaped filter 11 as shown in FIG. 1. To provide as much room as possible for the filter material 20 to fit inside the outer hollow tube 12, the actuating wire 14 preferably should be only thick enough to carry the force required to activate the filter assembly 10.

Referring to FIGS. 1 and 2a, distal to the filter housing 11 is a flexible atraumatic guidewire tip 30 consistent with current guidewire technology.

Figure 4:
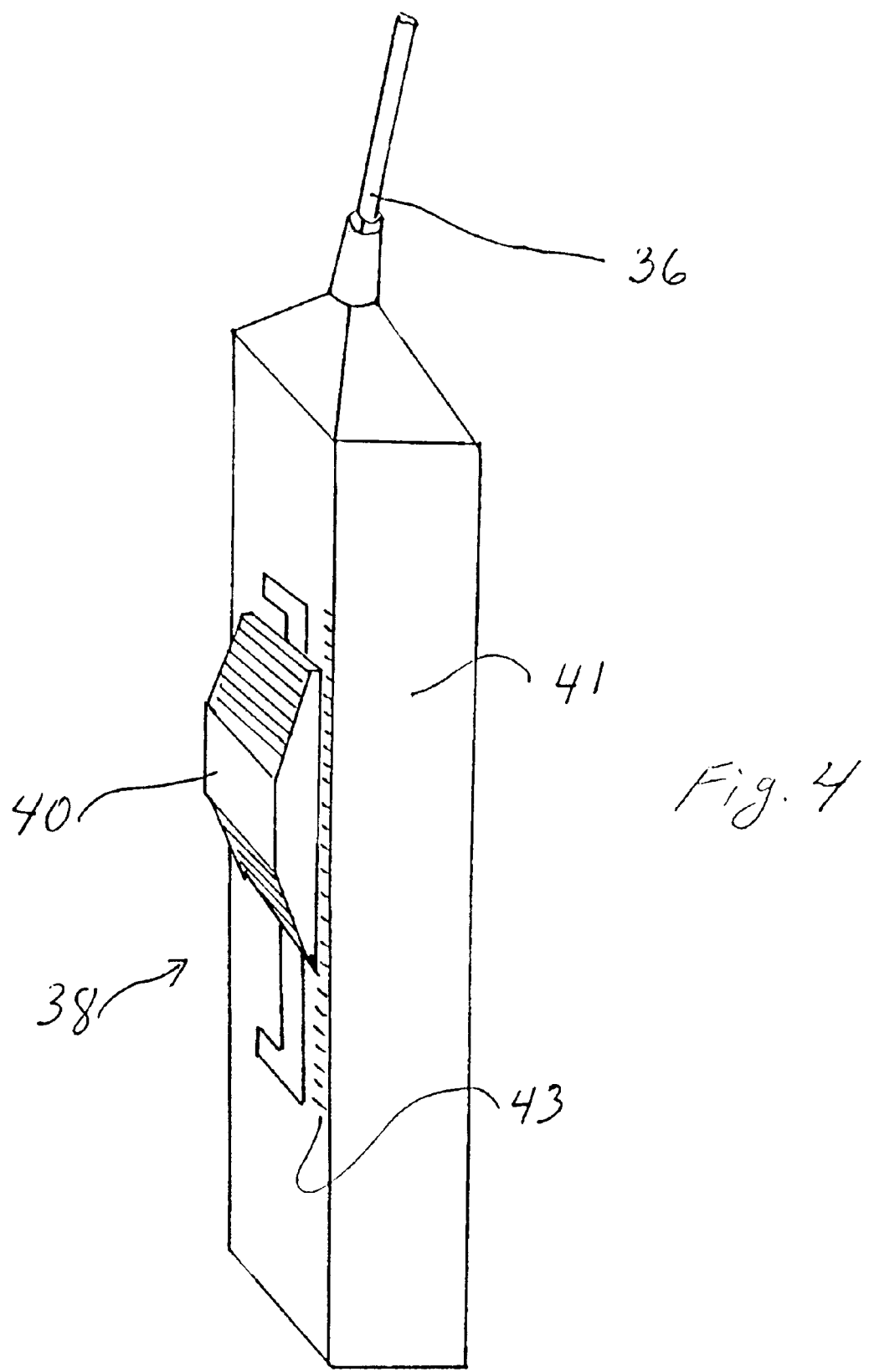
FIG. 4 is a partial side view of the proximal end of the guidewire filter device showing the guidewire remote activation handle.

Referring to FIG. 4, the proximal end 36 of the guidewire filter 10 is shown with a guidewire remote activation handle 38. The activation handle 38 may be removed so that the angioplasty balloon catheter may be placed over the guidewire filter 10 and positioned in the carotid artery. When attached, the activation handle 38 provides a means for pulling of the actuating wire 24 relative to the hollow tube 12 so that the filter basket 11 can be opened (and also closed) in an incremental fashion. The motion can be conveniently controlled by a ratcheting/locking mechanism 40 so that the physician has total control when opening and closing the filter basket 11. As noted above, radiopaque markers 19a, 19b, and 19c can be positioned on or adjacent to the rib portions to help the physician determine the relative state of expansion or contraction of the filter basket. Since the ratcheting/locking mechanism 40 is for pulling and pushing on the activation wire 24, its position relative to the casing 41can also provide the physician with information. Increment or calibration markers 43 can be formed on the casing 41 for this purpose as well. Since there may be cases wherein the physician would not want to completely collapse the filter basket 11 (e.g. if it is too full of collected embolic particles does not want to compress them too much), the ability to fairly well know the degree of expansion or contraction can be important.

Figure 5:
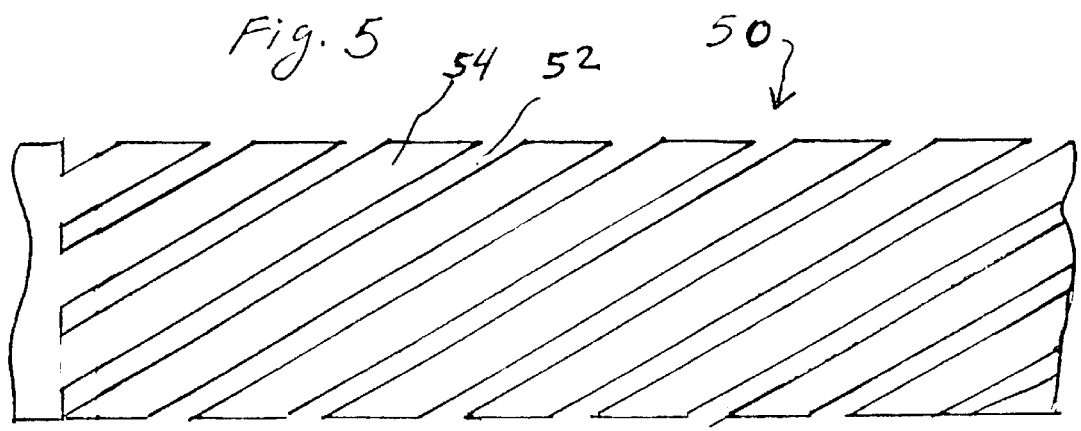
FIG. 5 is a partial side view showing a portion of a second embodiment of the invention wherein the guidewire filter portion of the device has spirally formed slots and rib portions.

In a second embodiment of the device 50, a portion of which is shown in FIG. 5, slots 52 are formed in a spiral orientation to create spirally oriented rib portions 54. As with the first embodiment of FIGS. 1–3, filter material (not shown) is attached to the inside of the rib portion.

Figure 6:
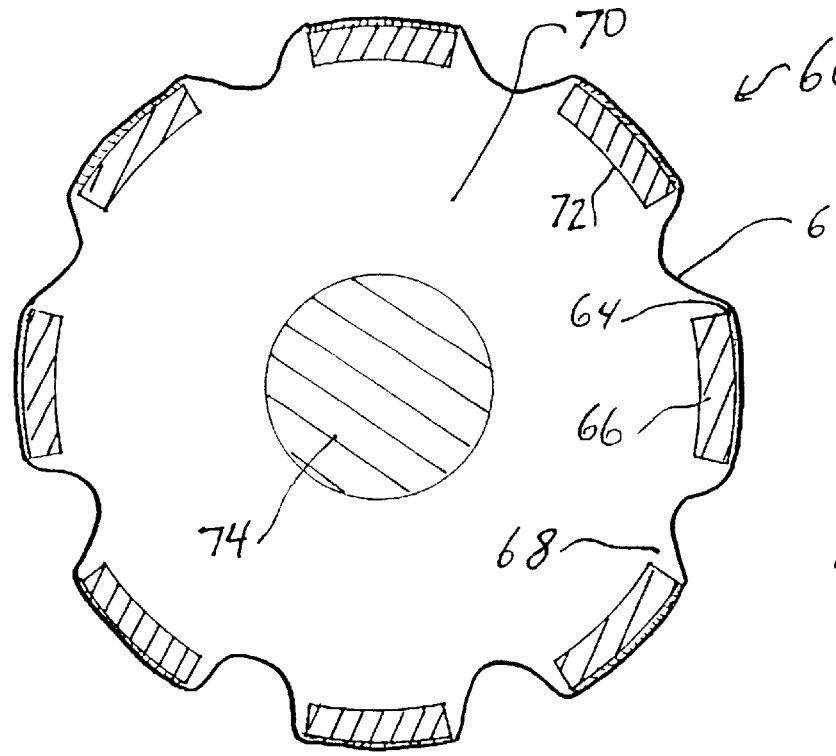
FIG. 6 is a cross-sectional view of a third embodiment of a guide filter device in a closed position wherein the filter material is affixed to the outside surface of the rib portions.

Turning to FIG. 6, a cross-sectional view of a third embodiment of a guide filter device 60 is shown in a closed position. In this embodiment, the filter material 62 is affixed (e.g. with adhesives, welding, sutures, mechanically, or by other known means) to an outside surface 64 of the rib portions 66. As in the first embodiment, the rib portions 66 are separated by slots 68. The filter material 62 can preferably comprise stretchable and resilient material to reduce or eliminate the need for folding of the filter material 62 into the space 70 between the inside surfaces 72 of the rib portions 66, and the actuating wire 74.

Figure 7:
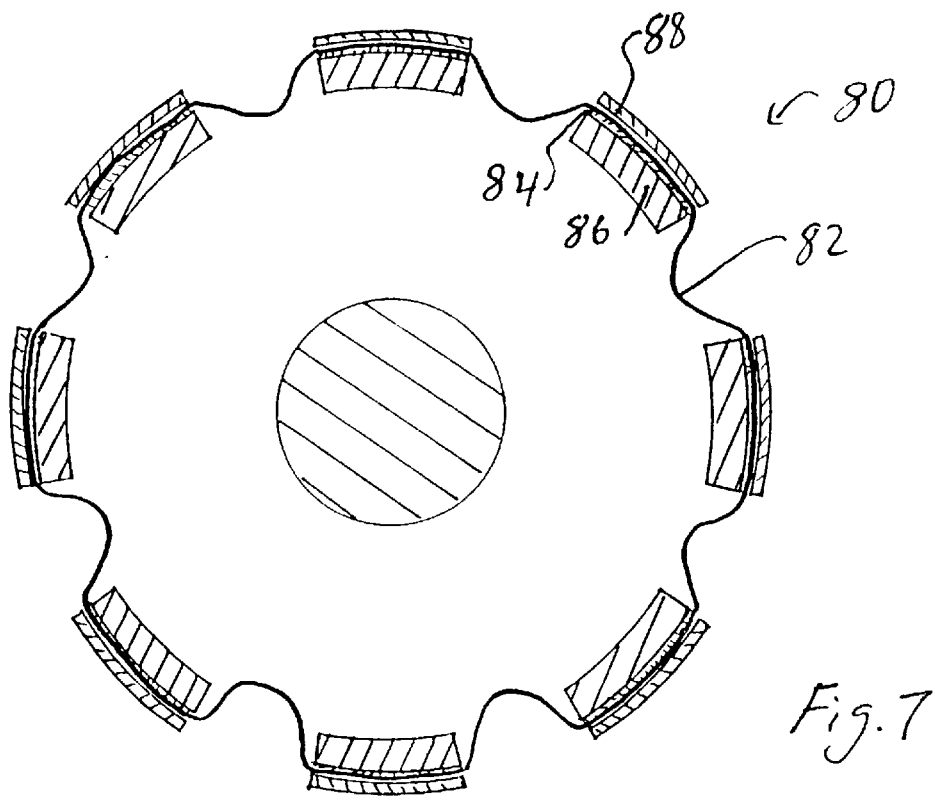
FIG. 7 is a cross-sectional view of a third embodiment of a guide filter device in a closed position wherein the filter material is sandwiched between an outside surface of the rib portions and rib cover portions to secure the filter material in place on the rib portions.

FIG. 7 is a cross-sectional view of a third embodiment of a guide filter device 80 in a closed position wherein the filter material 82 is sandwiched between an outside surface 84 of the rib portions 86 and a rib cover portions 88 affixed to the outside of the rib portions 86. The rib cover portions 88 can be secured with adhesives, welding, sutures, mechanical means (such as a snap fitting rib cover portions 88) to secure the filter material in place.

Figure 8:
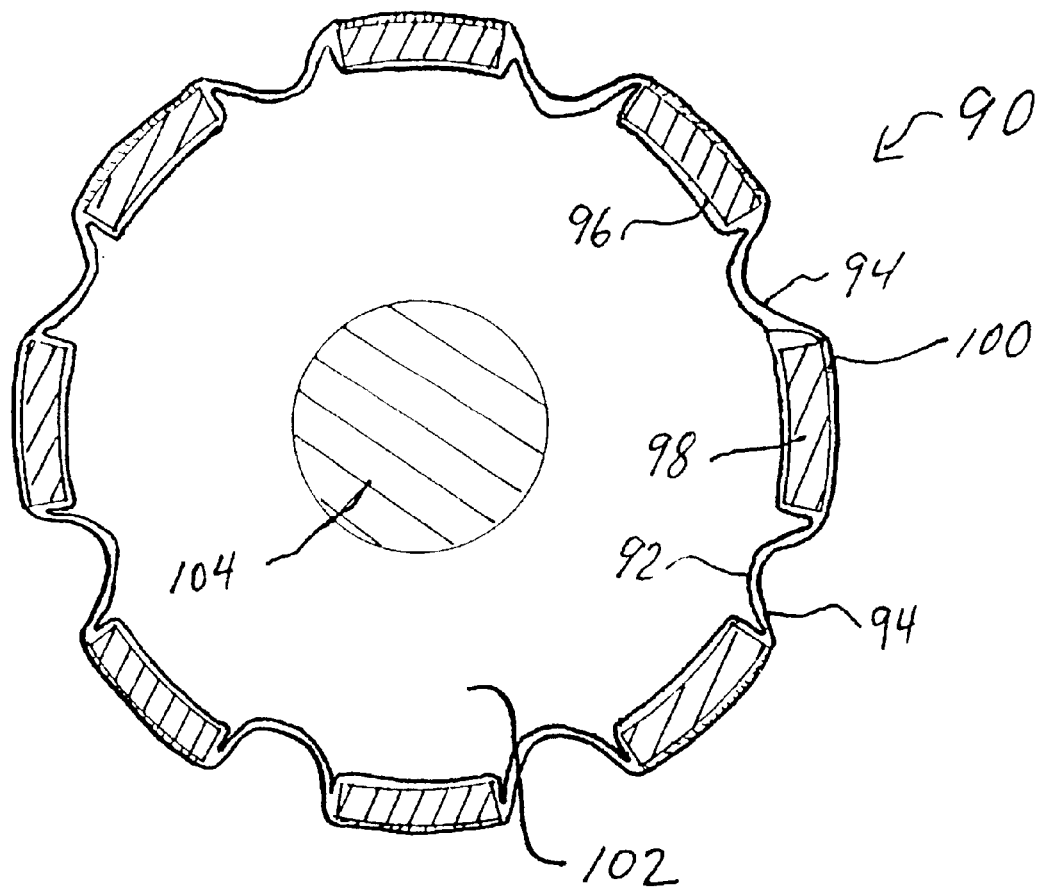
FIG. 8 is a cross-sectional view of a forth embodiment of a guide filter device in a closed portion that includes an inner and an outer section of filter material, wherein the rib portions are sandwiched between inner and outer sections of filter material.

FIG. 8 is a cross-sectional view of a forth embodiment of a guide filter device 90 in a closed position that includes an inner section of filter material 92 and a second, outer section of filter material 94. The inner section of filter material 92 is affixed to inner surfaces 96 of rib portions 98 (e.g. with adhesives, by welding, or other known means), and the second, outer section of filter material 94 is likewise affixed to outer surfaces 100 of rib portions 98 to thereby sandwich the rib portions 98 between the inner and outer sections of filter material 92 and 94. Use of two sections of filter material 92 and 94 permits thinner filter material to be used and disposed within the lumen 102 of the guidewire 90. As before, an actuating wire 104 is disposed in the lumen 102. The outer section of filter material 94 (as well as inner section of filter material 92) are preferably constructed of flexible, stretchable, elastic, and resilient material so that after tension is released on the actuating wire 104 in the lumen 112, the sections filter material 92 and 94 will provide extra force to help return the expanded rib portions 98 back to an undeployed state shown in FIG. 8.

Figure 9:
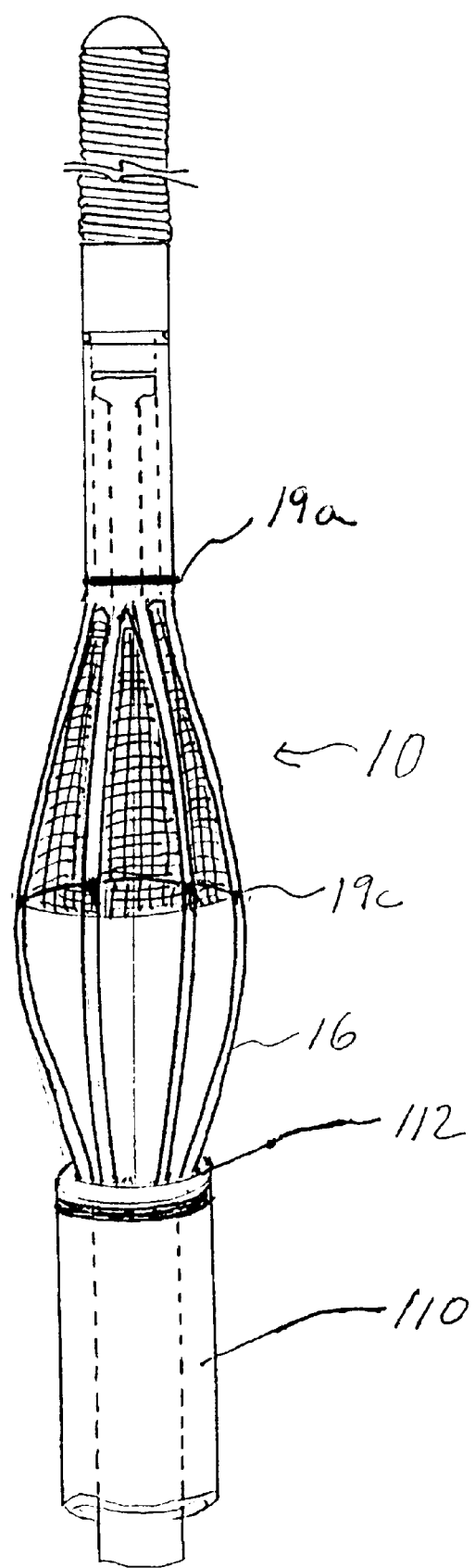
FIG. 9 is a partial perspective view of a first embodiment the invention protruding from the distal end of a guide tube or catheter with which the device is adapted to be utilized and with the guidewire partially retracted into the guide tube or catheter to assist in returning the rib portions and the filter material (filter basket) to the closed position.

Referring to FIG. 9, a partial perspective view is shown of the first embodiment the guidewire of the invention 10 and a guide tube 110. The guidewire 10 is shown protruding from the distal end 112 of the guide tube or catheter 110. Moving the guide tube (or a catheter) 110 distally forward and/or retracting the guidewire 10 into the guide tube or catheter 110 will cause the distal end 112 of the guide tube 110 to impinge on the proximal most confines of the rib portions 16 and will assist in returning the rib portions 16 and the filter material (filter basket 11) to the closed position thereby either partially or completely closing up of the filter basket 11. The distal end 112 of the guide tube or catheter 110 can optionally have a radiopaque marker 114, and when used in combination with optional radiopaque markers 19a, 19b, and/or 19c as shown in FIG. 2a (or radiopaque marked rib portions as shown in FIG. 2b) can be used to determine the relative position of the distal end 90 of the guide tube or catheter 92 to the filter basket 11.

While the device 10 has been discussed with particularly reference to its use in performing percutaneous carotid angioplasty procedures, it could be used in other applications where capture of embolic material is desirable. Also, at least in the area of the rib portions of the various embodiment of the device, the material will preferentially return to a straight and unexpanded shape when tension on the actuating wire is released.

The drawings and the foregoing description are not intended to represent the only form of the invention in regard to the details of this construction and manner of operation. In fact, it will be evident to one skilled in the art that modifications and variations may be made without departing from the spirit and scope of the invention. Although specific terms have been employed, they are intended in a generic and descriptive sense only and not for the purpose of limitation.

We claim:

1. A guidewire filter device, comprising:

an elongate hollow tube with a proximal end and a distal end, the hollow tube having an inside surface and an outside surface and defining a lumen formed therethrough, the hollow tube having a plurality of spaced apart elongate slots formed near the distal end, the plurality of slots defining a plurality of rib portions unitary with the hollow tube;

an actuating wire with a proximal end and a distal end, the distal end of the actuating wire being affixed to a point inside of the hollow tube that is distal to the rib portions; and filter material positioned within the lumen in the hollow tube with the filter material being affixed to portions of rib portions; whereby by pulling the proximal end of the actuating wire relative to the hollow tube, the rib portions will expand outwardly and open up the filter material in the form of a filter basket.

2. The guidewire filter device of claim 1, wherein the slots and rib portions are formed longitudinally in the hollow tube.

3. The guidewire filter device of claim 1, wherein the filter material is folded and is positioned in the lumen and is attached to the inside surfaces of the rib portions.

4. The guidewire filter device of claim 1, further comprising an activation handle on the proximal ends of the hollow tube and the actuating wire, the activation handle comprising a means for pulling of the actuating wire relative to the hollow tube so that the filter basket can be opened in an incremental fashion.

5. The guidewire filter device of claim 4, wherein the activation handle is detachably attachable to the proximal ends of the hollow tube and the actuating wire.

6. The guidewire filter device of claim 1, wherein the filter material is sized and positioned such that it is affixed to the inside surfaces of about the distal most half of the rib portions.

7. The guidewire filter device of claim 1, wherein the filter material is affixed to the inside of the rib portions with adhesive.

8. The guidewire filter device of claim 1, wherein the filter material comprises strechable and resilient material.

9. The guidewire filter device of claim 1, further comprising a flexible atraumatic guidewire tip.

10. The guidewire filter device of claim 1, wherein the slots and rib portions are formed in a spiral orientation in the hollow tube.

11. The guidewire filter device of claim 1, wherein the elongate hollow tube has an outer diameter that is 0.13 cm or smaller.

12. The guidewire filter device of claim 1, wherein the filter material is affixed to an outside surface of the rib portions.

13. The guidewire filter device of claim 12, further comprising rib cover portions that overlay the filter material on the rib portions.

14. The guidewire filter device of claim 7, further comprising a second, outer section of filter material that is affixed to outside surfaces of the rib portion.

15. The guidewire filter device of claim 1, further comprising radiopaque markers formed adjacent to proximal and distal ends of the rib portions.

16. The guidewire filter device of claim 1, further comprising radiopaque markers formed on the rib portions.

17. The guidewire filter device of claim 1, further comprising radiopaque material applied into or onto at least portions of the rib portions.

18. The guidewire filter device of claim 1, further comprising a guide tube through which the guidewire filter device is slideably positionable.

19. The guidewire filter device of claim 1, wherein at least in the area of the rib portions, the elongate hollow tube material comprises memory material which will tend to cause the rib portions to return to a straight and unexpanded shape.

* * * * *